United States Patent [19]

Leveen et al.

[11] Patent Number: 5,128,147

[45] Date of Patent: Jul. 7, 1992

[54] HEAT INTENSIFIER AND LOCALIZER FOR RADIOFREQUENCY THERMOTHERAPY

[75] Inventors: Harry H. Leveen; Eric G. Leveen, both of Charleston, S.C.; Robert F. Leveen, Philadelphia, Pa.

[73] Assignee: Thermal Developments, Inc., Las Vegas, Nev.

[21] Appl. No.: 563,206

[22] Filed: Aug. 6, 1990

Related U.S. Application Data

[63] Continuation of Ser. No. 294,005, Jan. 6, 1989, abandoned.

[51] Int. Cl.⁵ .................. A61K 9/16; A61K 9/50; A61K 33/32; A61K 33/26
[52] U.S. Cl. .................. 424/497; 424/639; 424/641; 424/643; 424/646
[58] Field of Search .......... 514/4; 424/497, 639, 424/641, 643, 646

[56] References Cited

U.S. PATENT DOCUMENTS 4,106,488 8/1978 Gordon .................. 424/1
4,154,246 5/1979 Leveen .................. 128/784
4,735,796 4/1988 Gordon .................. 424/9

FOREIGN PATENT DOCUMENTS 0005009 1/1986 Japan .

OTHER PUBLICATIONS

*United States Pharmacopeia,* 20th ed., U.S.P. Convention, Rockville, Md., 1980.
*The Radio Amateur's Handbook,* Amer. Radio Relay League, Newington, Conn., 1982.

Primary Examiner—Frederick E. Waddell
Assistant Examiner—Diane Gardner
Attorney, Agent, or Firm—John S. Hale

[57] ABSTRACT

A sterile injectable mixture which intensifies and localizes radio frequency thermotherapy; the injectable mixture contains finely ground ferrite particles in a viscid aqueous suspension, the ferrite being matched for maximum radio frequency absorption at a specific frequency. A chemotherapeutic agent, a surfactant and a bioacceptable hydrophic colloid are also contained in the mixture.

12 Claims, No Drawings

HEAT INTENSIFIER AND LOCALIZER FOR RADIOFREQUENCY THERMOTHERAPY

This is a continuation of application Ser. No. 294,005 filed Jan. 6, 1989, now abandoned.

BACKGROUND OF THE INVENTION

Hyperthermia has proven to be useful in the treatment of malignant tumors. (JAMA 1976 235:2198; U.S. Pat. No. 3,991,770; U.S. Pat. No. Re. 32,066) Heat more than doubles the ability of chemotherapy to destroy malignant tumors and enhances the therapeutic index of chemotherapeutic agents. (J. Nat. Cancer Inst. 1982 68:487 Cancer Res. 1974 34:3117) Heat also enhances the treatment effect of ionizing radiation in treating tumors. (Applied Radiol. 1984 13:150 Cancer Res Suppl. 1984 44:471 4s) Although heat by itself is lethal to cancer cells, especially those in the anoxic tumor center, therapy with heat alone required that the tumor be rapidly raised to temperatures of 43 C. and remain at these temperatures for 2 to 3 hours. When tumors are slowly heated the cells become more thermoresistant and the killing effect of the heat is reduced in effectiveness. Because it is usually not possible to raise the whole body temperatures to 43 C. and maintain this temperature without serious and even fatal damage to normal cells, generalized body hyperthermia is less effective than localized hyperthermia and requires continuous observation and management by a team of several physicians. Rarely, is the systemic temperature raised higher than 42 C. At these temperatures serious coagulation defects in the blood occur. Other hazards to patients are malignant hyperthermia and brain damage. Generalized systemic hyperthermia requires a specialized team of physicians and is accompanied by serious risk. Therefore, most physicians prefer localized hyperthermia of the cancer itself.

The simplest method to induce such localized hyperthermia is by radiofrequency. Microwaves, which can easily be focused to the cancerous target are rapidly absorbed by passage through the intervening tissue. Absorption by body tissues reduces the amount of heat which can be generated in the tumor. Fifty percent of the microwaves are absorbed during the passage through the first 3 to 5 centimeters of tissue depending on the frequency. The power is so attenuated in the superficial tissues that microwaves cannot be successfully used to heat deep tumors. Therefore, longer wave lengths that are not as readily absorbed must be used to bring about temperature sufficiently high to treat deep tumors. However, a dilemma arises in that longer wavelengths cannot be focused and thereby be directed to the cancerous target. Previous experience has shown that power can be concentrated by an R.F. circuit which is properly tuned to the resonant frequency of a therapeutic RF generator at 13.56 mHz or 27.12 mHz. (U.S. Pat. No. 4,154,246) However, unless a tumor is located in a hollow viscus, it is necessary to surgically implant such resonant circuits which involves a major operative procedure for the patient. The present invention details a simple method for enhancement of RF heating not requiring surgery or the expense of tuned LC circuits.

In the past, iron needles have been used to concentrate heating of tissues. This was usually accomplished by placing stainless steel needles into the tumor mass and heating the needles by induction. The method entails the placement of multiple needles into the tumor and removing them after therapy. While such a procedure may be effective with superficial tumors it is not appropriate with deep tumors because of the long lengths of metal which extend out into the normal tissue and the difficulties involved in placing the needles. Also, needles cannot be allowed to extend from the lung across the plural space and exit from the skin. Such a procedure would bring about the leakage of air from the alveoli into the plural space and result in a serious condition known as pneumothorax. Large caliber needles would be required to provide adequate surface area for heating. Iron filings undergo corrosion in the tissues and cause necrosis. Of the various metals investigated in the form of a spheres (1/16 in. diameter) carbon steel has proved to be the most efficient followed by stainless steel. Nonetheless, these metals must be properly oriented in the energy field. If the metal in the form of a rod is parallel to the field, the maximum heating takes place but if it is perpendicular to the field no heating takes place at all. (J. Biomed. Materials Res. 1976 10:327) For all of these reasons, the introduction of a metal, even in powdered from, is generally unsatisfactory. Others have used pellets and seeds of copper and nickel but these must also be implanted. (Radiology 1986 154:243)

SUMMARY OF PRESENT INVENTION

The present invention uses a finely ground ferrite having its maximum radio frequency absorption in the region of 27 megaHertz, the frequency of the RF generator. If other frequencies are used, the ferrite is matched for absorption at that frequency. Ferrite absorbs RF energy and is itself heated by hysteresis. Since these compounds usually have a high dielectric constant they are heated by induction only slightly if at all. The higher the radiofrequency, the more heat that is generated by induction heating of body tissues. For this reason, 13.56 mHz generates half the amount of heat generated by 27.12 mHz. The gain in heating at 27.12 mHz far outweighs the slight advantage of reduced tissue absorption at 13.56 mHz. Ferrite also gives off radiation and in this respect acts like a radio receiver and retransmitter.

The ferrite is a ceramic like material and is finely ground for use in the invention. The finely ground ferrite is suspended in a viscid aquous medium. The small size of the particles and the viscosity of suspending medium impedes rapid settling from the aqueous suspension according to Stoke's Law. This makes it possible to infiltrate the ferrite suspension into the tumor tissue with a needle and a syringe. Chemotherapeutic agents may be added to the suspension mixture to insure that the chemotherapeutic agent will reach the target organ in appropriately high concentrations. (Am. Surgeon 1984 50:6165) The injection of the ferrite can be appropriately directed with radiological guidance utilizing a CT scan. The finely ground ferrite powder can be encapsulated with a biologically inert plastic material which will further insure biocompatability of the ferrite.

DETAILED DESCRIPTION OF INVENTION

Ferrite is a crystalline complex, usually man made, which possesses a spinel structure and consists essentially of ferric oxide and at least one other metallic oxide which is usually, although not always, divalent in nature. The crystals usually contain $\frac{2}{3}$ iron and $\frac{1}{3}$ other metallic ions. Ferrites are characterized by high magnetic permeability. These compounds are prepared by ceramic techniques in a refractory oven. Ferrites are commonly used to form ceramic magnets which are often used in the electronic industry and in the construction of electrical motors especially induction motors. The term now usually includes any oxidic magnetic material. (Bailsford Magnetic Materials John Wiley, N.Y. 3rd ed. 1960; Gray "Oxide Spinels" in High Temperature Oxides, Part IV ed. by A. M. Alper Acad. Press N.Y. 1971)

In accordance with the invention, the ceramic ferrite with the proper absorption properties is placed in a ball mill and ground to an extremely fine powder. The finely ground powder is mixed with a hydrophilic colloid such as sodium alginate, dextran, carbowax, or other appropriate hydrophillic colloids which are approved for parenteral injection. A mild surfactant such as a lecithin, a non-ionic detergent, or a hydroxycellulose is added to promote wetting of the ferrite and easy suspension on shaking. The individual ferrite particles may be coated by microencapsulation with an inert plastic such as para-di-zylene manufactured by Union Carbide and sold under the trade name of Parylene. A water absorbing colloid can be added as a secondary coating. Nonetheless, it has been found that such coatings are unnecessary since the ferrites are insoluble in animal tissues and produce only a moderate fibrous tissue response which may be beneficial in causing cicatrization of a malignant lesion.

EXAMPLE

Phantoms of human tissue can be constructed with an aqueous solution of agar containing small amount of sodium chloride. The agar is dissolved in hot water and solidifies upon cooling. The electrical properties of these phantoms were made to mimic the absorption coefficients to RF at 27.12 mHz for tissue such as a lung, muscle, or even fatty tissue. If these phantoms are constructed so that they can be rapidly split into two halves, the interior temperatures can be measured or scanned to show the distribution of temperatures in the interior of the phantom. When such phantoms, containing the finely ground ferrite in the center of the phantom, are exposed to a magnetic field of high density RF at 27.12 mHz, the energy; the heat, which is developed in the phantom, is concentrated in the region containing the ferrite powder. Temperatures were measured using a Bofors thermograph. The distribution of heat was measured by splitting the phantom and scanning its interior with the thermograph. If one measures the distribution of RF in air with an ammeter connected to a wire loop it can be seen the magnetic liens of force are deflected toward the ferrite. The increased heating therefore is due to hysteresis in the ferrite and an increase in induction heating by concentrating the magnetic lines of force toward the ferrite.

In actual use the ferrite is combined with a chemotherapeutic agent contained in a local anesthetic such as lidocaine or procaine. The mixture is injected into the tumor through a 21 gauge needle using a total of about 10-15 cc of the mixture containing 5 grams of ferrite. The entire tumor is infiltrated with the mixture and heat therapy begun immediately thereafter. On subsequent therapy sessions only chemotherapy and an anesthetic agent is used. Total destruction of the tumor is achieved in 4 therapy sessions. A rest period of 4 to 8 weeks is allowed before the patient is reevaluated for further therapy.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A sterile injectable mixture for injection into a tumor which intensifies and localizes radio frequency thermotherapy of the tumor, said mixture comprising the combination of finely ground manganese zinc ferrite means in an aqueous suspension, a surfactant, a chemotheraputic agent, an anesthetic agent and a thickening agent, said manganese zinc ferrite means comprising individual manganese and zinc complexed ferrite particles coated by microencapsulation with an inert plastic para-di-zylene.

2. A sterile injectable mixture as claimed in claim 1 wherein said aqueous suspension is in a saline solution.

3. A sterile injectable mixture as claimed in claim 1 wherein said aqueous suspension is a bioacceptable hydrophillic colloid.

4. A sterile injectable mixture as claimed in claim 3 wherein said hydrophillic colloid is sodium alginate.

5. A sterile injectable mixture as claimed in claim 3 wherein said hydrophillic colloid is dextran.

6. A sterile injectable mixture as claimed in claim 3 wherein said hydrophillic colloid is carbowax.

7. A sterile injectable mixture as claimed in claim 1 wherein said surfactant is lecithin.

8. A sterile injectable mixture as claimed in claim 1 wherein said surfactant is a non ionic detergent.

9. A sterile injectable mixture as claimed in claim 1 wherein said surfactant is a hydroxycellulose.

10. A sterile injectable mixture as claimed in claim 1 wherein said anesthetic agent is lidocaine.

11. A sterile injectable mixture as claimed in claim 1 wherein said anesthetic agent is porcaine.

12. A sterile injectable mixture for injection into a tumor which intensifies and localizes radio frequency thermotherapy, said mixture containing finely ground complexed manganese zinc ferrite particles in powder form, said complexed manganese zinc ferrite particles being at least two thirds iron and encapsulated in biologically inert plastic material in a viscid aqueous suspension, said complexed manganeses zinc ferrite particles being matched for maximum radio frequency absorption ranging from 13.56 mHz to about 27.12 mHz and substantially totally absorbing the energy of the radio frequency waves, said mixture further containing a chemotherapeutic agent, a surfactant and a bioacceptable hydrophillic colloid.

* * * * *